United States Patent [19]
Redlich et al.

[11] Patent Number: 5,225,279
[45] Date of Patent: * Jul. 6, 1993

[54] SOLVENT CORE ENCAPSULANT COMPOSITION

[75] Inventors: George H. Redlich, Norristown; Ronald W. Novak, Chalfont, both of Pa.

[73] Assignee: Rohm and Haas Company, Philadelphia, Pa.

[*] Notice: The portion of the term of this patent subsequent to Jan. 15, 2008 has been disclaimed.

[21] Appl. No.: 606,224

[22] Filed: Oct. 31, 1990

Related U.S. Application Data

[63] Continuation of Ser. No. 942,312, Dec. 16, 1986, Pat. No. 4,985,064, which is a continuation of Ser. No. 728,992, Apr. 30, 1985, Pat. No. 4,667,003.

[51] Int. Cl.$^5$ ............... A01N 43/02; B01J 13/18; C08F 265/04
[52] U.S. Cl. ............... 428/402.22; 504/116; 71/DIG. 1; 264/47; 424/408; 427/213.34; 428/402.24; 428/407; 514/963; 523/122; 525/301; 525/902; 525/911
[58] Field of Search ............... 264/4.7; 427/213.34; 428/402.24, 407, 402.22; 525/301, 902, 911; 71/90, 124, DIG. 1; 424/408; 523/122

[56] References Cited

U.S. PATENT DOCUMENTS

| 2,873,263 | 2/1959 | Lal | 523/122 X |
| 3,655,591 | 4/1972 | Seiner | 521/139 X |
| 3,950,284 | 4/1976 | Fukuda et al. | 525/301 X |
| 3,959,895 | 6/1976 | Lonning | 524/296 X |
| 4,427,836 | 1/1984 | Kowalski et al. | 524/460 X |
| 4,468,498 | 8/1984 | Kowalski et al. | 525/301 |
| 4,469,825 | 9/1984 | Kowalski et al. | 524/812 X |
| 4,710,525 | 12/1987 | Kraemer et al. | 525/902 X |
| 4,985,064 | 1/1991 | Redlich et al. | 71/90 |

FOREIGN PATENT DOCUMENTS 0158268  9/1982  Japan ............... 523/122

Primary Examiner—Richard D. Lovering
Attorney, Agent, or Firm—Brian W. Stegman

[57] ABSTRACT

The present invention relates to a sequential polymerization process for preparing a water-insoluble dispersion of core/shell particles. In one embodiment the process may be employed to produce a particulate dispersion useful in making water-based coating compositions wherein on drying the particulate dispersion serves as an opacifying agent. In another embodiment the process may be employed to microencapsulate a hydrophobic target material, such as a biocide or herbicide.

1 Claim, No Drawings

SOLVENT CORE ENCAPSULANT COMPOSITION

This is a continuation of application Ser. No. 942,312, filed Dec. 16, 1986, now U.S. Pat. No. 4,985,064, which is a continuation of Ser. No. 728,992, filed Apr. 30, 1985 and now U.S. Pat. No. 4,677,003

BACKGROUND OF THE INVENTION

1. Field of the Invention

The present invention relates to both the coatings and microencapsulation arts and specifically to a sequential polymerization process for preparing a water-insoluble dispersion of core/shell particles. In one embodiment the process may be employed to produce a particulate dispersion useful in making water-based coating compositions wherein on drying the particulate dispersion serves as an opacifying agent. In another embodiment the process may be employed to microencapsulate a hydrophobic target material, such as a biocide or herbicide.

2. Brief Description of the Prior Art

Microvoid containing particles have previously been prepared by a variety of techniques.

For example, Kershaw, et al., U.S. Pat. No. 3,891,577, prepares a vesiculated polymer by converting to a solid polymer, a liquid medium containing dispersed therein particles of another polymer swollen by a liquid swellant, the liquid swellant then being at least partially removed from the dispersed polymer particle. The liquid medium may be converted to a solid by removal of solvent, e.g., from a solution of the solid polymer, or preferably, by polymerization of a monomer, comonomers, or an oligomer or a mixture of these. Optionally, a dissolved polymer may be present in the liquid to be polymerized. Solidification of the liquid in which these swollen particles are dispersed and removal of the swellant is then carried out to provide the vesiculated polymer, which may be in bulk form, as a film, or in the form of a coating applied to a substrate.

In another embodiment, Kershaw teaches that the dispersion of swollen polymer in the liquid medium may itself be dispersed in a further liquid in which it is insoluble. The further liquid is referred to as the suspending liquid. Solidification of the medium is then carried out and after separation of the granules formed from the suspending liquid, liquid swellant may be removed from the swollen polymer to provide vesiculated polymer in granular form. Alternatively, when, for example, the vesiculated granules are to be used in a coating composition with which the suspending liquid is compatible, the granules formed by solidification of the medium may be incorporated into the composition as a slurry in at least part of the suspending liquid. On applying the composition to a substrate, formation of a coating film and removal of swellant from the swollen dispersed polymer to form the vesicles within the granule then take place concurrently.

Kurth, et al., in U.S. Pat. No. 3,870,099, disclose the preparation of sequential acrylic polymers containing 0.5-2.5% of an alpha, beta-unsatruated carboxylic acid. The bulk of the acid is introduced in the early part of the polymerization.

Kowalski et al., in U.S. Pat. No. 4,427,836, disclose the production and use of water-insoluble particulate heteropolymers made by sequential emulsion polymerization in dispersed particles of which a core of a polymeric acid is at least partially encased in a sheath polymer that is permeable to a volatile base, such as ammonia or an organic amine, adapted to cause swelling of the core by neutralization. The sheath is not permeable to permanent, non-volatile bases such as sodium hydroxide. The aqueous dispersion of the acid-containing core/sheath particles is useful in making water-based coating composition wherein it may serve as an opacifying agent when the volatile base is used to at least partially neutralize the heteropolymer, microvoids being formed in cores of the swollen particles and the film during the drying. Although the core may be made in a single stage of the sequential polymerization and the sheath may be the product of the single sequential stage following the core stage, the making of the core component may involve a plurality of steps in sequence followed by the making of the sheath which also may involve a series of sequential steps. Thus the first stage of the emulsion polymerization in the process of the Kowalski invention may be the preparation of a seed polymer containing small dispersed polymer particles insoluble in the aqueous emulsion polymerization medium. This seed polymer, which may or may not contain any acid component, provides particles of minute size which form the nuclei on which the core polymer of acid monomer, with or without nonionic comonomers, is formed. The polymer particles of this invention are prepared by aqueous emulsion polymerization, which requires a water-soluble free radical initiator, or a mixture of such an initiator with a water-soluble reducing agent to form a redox system. In a preferred embodiment a seed polymer is used along with a low level of core stage emulsifier. By carrying out the emulsion polymerization while maintaining low levels of emulsifier, the subsequent stages of polymer formation deposit the most recently formed polymer on the existing dispersed polymer particles resulting from the preceding step or stage. If the amount of emulsifier is kept below the amount corresponding to the critical micelle concentration (CMC) for a particular monomer system, a preferred unimodal product results. While the CMC may be exceeded somewhat without the formation of an objectionable or excessive number of dispersed micelles or particles, it is preferred that the number of micelles during the various stages of polymerization be controlled so that the deposition of the subsequently formed polymer in each stage occurs upon the dispersed micelles or particles formed in the previous stages.

Kowalski et al., in related U.S. Pat. No. 4,469,825, disclose core/sheath polymer particles wherein the core monomer system requires an amine group-containing comonomer which comprises at least 5% by weight of the core monomer system.

Kowalski et al., in U.S. Ser. No. 590,082, filed Mar. 15, 1984, and now abandoned disclose a process for making core/sheath polymer particles in which the emulsion polymerized core system may contain either a polymerizable carboxylic acid and/or amine, giving an acid or base functional core, and in which the sheath monomer system comprises monomers having no ionizable group. A hydrophobic material such as material selected from the silicone surfactants, fluorocarbon surfactants, and hydrophobic non-vinyl polymerizable liquids, is employed in the polymerization process.

Blankenship et al., in U.S. Ser. No. 690,913, filed Jan. 11, 1985, and now U.S. Pat. No. 4,594,363 disclose a process for making core/sheath polymer particles useful for opacifying coating films, comprising (A) emulsion polymerizing a core from a core monomer system comprised of at least one ethylenically unsaturated monomer containing acid functionality;

(B) encapsulating the core with a hard sheath by emulsion polymerizing a sheath monomer system in the presence of the core, the sheath permitting penetration of fixed or permanent bases;

(C) swelling at elevated temperature the resultant core-sheath polymer particles with fixed or permanent base so as to produce a dispersion of particles which, when dried, contain a microvoid which causes opacity in compositions in which they are contained, provided that either (1) the sheath comprises at least about 1% acid functional monomer or (2) the swelling takes place in the presence of solvent.

Kowalski et al., in U.S. Pat. No. 4,468,498, discloses a process for making an aqueous dispersion of core/sheath polymers in which the core contains sufficient acid groups to render the core swellable by neutralization with a volatile base to at least twice its volume and wherein the sheath is permeable to the base.

Morehouse, Jr. et al., in U.S. Pat. No. 4,049,604, disclose aqueous dispersions of normally solid, organic polymeric particles that are prepared by (1) dispersing an oil phase containing at least one emulsion polymerizable monomer such as styrene in an aqueous phase containing a stabilizing emulsifier such as sodium dodecylbenzene sulfonate and a copolymer of a sulfo ester of an alpha, beta-ethylenically unsaturated carboxylic acid, such as 2-sulfoethyl methacrylate, and butyl acrylate and (2) subjecting the dispersion to emulsion polymerization. Microspheres having liquid centers and seamless rigid walls of the normally solid, organic polymer are prepared according to this method except that the starting oil phase also contains a nonpolymerizable, water-insoluble liquid such as hexane. The polymers of sulfo esters of alpha, beta-ethylenically unsaturated carboxylic acids serve as coalescence aids. The diameter of the resulting microspheres is inversely related to the concentration of the polymer of sulfo ester employed (operable range: 0.2 to 2.0 weight percent). Microspheres by this process have an average diameter of from about 0.5 to about 3 microns, when the amount of sulfoester employed is at the upper end of the acceptable range. Microspheres of this size are suspensions and not dispersions, they will settle out of the aqueous medium on standing.

Ugelstad, in U.S. Pat. No. 4,336,173, discloses a process for preparing an aqueous emulsion or dispersion of a partly water-soluble material and optionally further conversion of the prepared dispersion or emulsion to a polymer dispersion when the partly water-soluble material is a polymerization monomer. In the first step a dispersion of polymer particles is prepared containing one or more materials having very low solubility in water, then in a second step there is added the partly water-soluble material which diffuses into the particles from the first step, and then, if the partly water-soluble material is a polymerizable monomer, polymerization may be affected. By using a seed consisting of a polymer and essentially water-insoluble material, the seed particles will be capable of absorbing much greater amounts of monomer, it often being possible to add all the monomer in one step, and the amount of seed employed may be greatly reduced, in comparison with conventional emulsion seeded polymerization. In the conventional process, the seed particles consists of polymer molecules which are capable of absorbing only one to four times their own volume in polymerizable monomer; however, the Ugelstad seed can absorb much greater amounts of monomer. Thus the tendency to form a second mode of unseeded polymer particles during the polymerization of the monomer swollen seeds is reduced. Either a water-soluble initiator such as potassium persulfate or hydrogen peroxide or an oil-soluble initiator such as lauryl peroxide may be employed.

Ugelstad, in U.S. Pat. No. 4,113,687, discloses a process for preparing a latex by efficiently homogenizing an aqueous mixture containing an emulsifier and a water-insoluble solvent for the monomer to be polymerized, adding monomer and, if desired, further water to the homogenized mixture and also water-soluble polymerization initiator. Instead of a water-soluble initiator, an oil soluble initiator may be used provided it has sufficient solubility diffused through the aqueous phase into the drops of water insoluble solvent and monomer.

Microencapsulation methods and the properties of the resulting microcapsulates are reviewed by T. Kondo in *Surface and Colloid Science*, Volume 10 (Plenum Press, New York 1978) pp. 1–41. Microencapsulation is also reviewed by R. E. Sparks in Kirk-Othmer, *Encyclopedia of Chemical Technology*, Volume 15 (3rd Edition) pp. 470–492. Microencapsulation of water immiscible materials, such as aqueous dispersions of pesticides and herbicides, is reviewed by Beestman et al. in U.S. Pat. Nos. 4,417,916 and 4,280,833, in which an improved microencapsulation process employing lignin sulfonate emulsifier and the reaction of polymethylene polyphenylisocyanate and a polyfunctional amine is taught. R. C. Koestler, in U.S. Pat. No. 4,360,376, teaches an interfacial polycondensation method of microencapsulating trifluralin, a pre-emergent herbicide. H. B. Scher et al., in U.S. Pat. No. 4,155,741, discloses a stable suspension-buffer system for aqueous suspensions of polyurea-microencapsulated materials, including herbicides and insecticides, which can be obtained by using aluminum hydroxide or ferric hydroxide as suspending agent, thereby preventing separation and caking in flowable microcapsule formulations.

SUMMARY OF THE INVENTION

The present invention provides an improved process for producing aqueous dispersions of polymeric core/shell particles prepared by sequential microsuspension polymerization having a core containing a solvent blend. These particles are useful in opacifying film formed by aqueous coating compositions through microvoid formation. This invention also provides an improved process for microencapsulation of organic target materials in an aqueous dispersion of water-insoluble core/shell particles. Because an aqueous medium is employed rather than an organic solvent for the preparation of the microcapsule walls, the aqueous dispersions of microencapsulated target materials may be advantageously used directly in many applications, such as in preparing for agricultural use aqueous tank mixes of encapsulated pesticides and non-encapsulated fertilizer. These and other advantages of the present invention, which will be apparent from the disclosure below, are met by the present invention, which is a process for preparing an aqueous dispersion of water-insoluble core/shell particles comprising (a) preparing core emulsion by emulsifying in water at high shear
    (1) at least one hydrophilic solvent,
    (2) at least one hydrophobic solvent, (3) initial monomer comprising at least two polymerizable mono-alpha, beta-ethylenically unsaturated compounds wherein said initial monomer includes from about 2 to 4% by weight, based on the total weight of said initial monomer of alpha, beta-ethylenically unsaturated carboxylic acid monomer, (4) anionic surfactant (5) water-insoluble emulsion stabilizer, and (6) water-insoluble thermal polymerization initiator, wherein said hydrophobic and hydrophilic solvents are non-solvents for a polymer prepared by polymerizing said initial monomer, (b) heating said core emulsion to polymerize said initial monomer, thereby forming core particles, (c) adding at least one base selected from ammonia and the organic amines thereby neutralizing polymerized carboxylic acid and forming core/shell particles, and (d) optionally adding additional monomer whereby said additional monomer is polymerized on said core/shell particles.

DETAILED DESCRIPTION OF THE INVENTION

The present invention is directed to a process for polymerization employing an oil-soluble polymerization initiator, such as lauryl peroxide. Because an oil-soluble initiator, as opposed to an initiator soluble in water or slightly soluble in water is employed, the process can be referred to as a suspension polymerization technique as opposed to an emulsion polymerization process. The oil-soluble initiator, a mixture of hydrophobic and hydrophilic solvents, anionic surfactant, and water-insoluble emulsion stabilizer are emulsified in water at high shear along with initial monomer which comprises at least two polymerizable mono-ethylenically unsaturated compounds to form a "core" emulsion. When it is desired to encapsulate an organic target material, such as a biocide or herbicide, the target material is included in the mixture which is sheared to yield the core emulsion. The organic target material may be substituted for the hydrophobic solvent, or a mixture of hydrophobic solvent and organic target materials may be used. The hydrophilic and hydrophobic solvents and the mixture are nonsolvents for the polymer which is prepared by polymerizing the initial monomer. The initial monomer includes from about 2% to 4% by weight, based on the total weight of the initial monomer, of alpha, beta-ethylenically unsaturated carboxylic acid monomer. The core emulsion is then heated to polymerize the initial monomer. Subsequently at least one base selected from ammonia and the organic amines is added to the dispersion, thereby neutralizing the polymerized carboxylic acid and developing the core/shell structure of the particles. Subsequently, optional additional ethylenically unsaturated monomer is added to the core/shell particle dispersion.

It is believed that neutralization of the carboxylic acid induces polymer carrying carboxylic acid functionality to migrate to the interface between the aqueous medium and the core particles, creating a core/shell structure within the particles. However, the present invention is in no way limited by this explanation. The additional monomer is polymerized on or in the previously formed shell of the core/shell particles, the polymerization of the additional monomer being initiated by residual water-insoluble thermal polymerization initiator within the already formed core/shell particles.

In an alternative embodiment, additional initiator may be added to the aqueous dispersion of core particles prior to the addition of the additional monomer. The additional polymerization initiator may also be added concurrently with or subsequently to the addition of the additional monomer. The additional polymerization initiator may be water insoluble, slightly water soluble or water soluble. When it is desired to avoid or minimize the formation of a second mode of polymer particles, polymerization of the additional monomer in the absence of additional polymerization initiator is preferred. It is preferred that the additional monomer composition be chosen so that additional monomer when polymerized forms a shell upon the pre-existing core particles. Examples of additional polymerization initiators which may be employed include polymerization initiators of the free radical type, such as ammonium or potassium persulfate, which may be used alone or as the oxidizing component of a redox system, which also includes a reducing component such as potassium metabisulfite, sodium thiosulfate or sodium formaldehyde sulfoxylate. The reducing component is frequently referred to as an accelerator. The initiator and accelerator, commonly referred to as catalyst, catalyst system or redox system, may be used in proportion from about 0.01% or less to 3% each, based on the weight of monomers to be copolymerized. Examples of redox catalyst systems include t-butyl hydroperoxide/sodium formaldehyde sulfoxylate/Fe(II), and ammonium persulfate/sodium bisulfite/sodium hydrosulfite/Fe(II). The polymerization temperature may be from room temperature to 90° C., or more, and may be optimized for the catalyst system employed, as is conventional.

Chain transfer agents including mercaptans, polymercaptans and polyhalogen compounds are sometimes desirable in the polymerization mixture to moderate polymer molecular weight. Examples of chain transfer agents which may be used include long chain alkyl mercaptans such as t-dodecyl mercaptans, alcohols such as isopropanol, isobutanol, lauryl alcohol or t-octyl alcohol, carbon tetrachloride, tetrachloroethylene and tricholorobromaethane. Generally from about 0 to 3% by weight, based on the weight of the monomer mixture, may be used.

If desired, the addition and polymerization of the additional monomer may be omitted, provided that the initial monomer is selected to yield polymer having a calculated glass transition temperature ($T_g$) greater than about 70° C. Even when additional monomer is employed and is polymerized on core/shell particles, it is preferred that the core/shell particle polymer have a calculated $T_g$ greater than about 70° C. The $T_g$ of a polymer with a specific monomer composition is determinable in a known manner either experimentally or by calculation. The method of calculating the $T_g$ based upon the $T_g$ of homopolymers of individual monomers is described by Fox, *Bull. Am. Physics Soc.* 1,3, pg. 123 (1956). Monomers may be selected to obtain the appropriate $T_g$ through use of the "Rohm and Hass Acrylic Glass Transition Temperature Analyzer", Publication CM-24 L/cb of Rohm and Hass Company, Philadelphia, PA. Examples of initial monomers which when polymerized will yield core polymer having a calculated $T_g$ greater than about 70° C. are methyl methacrylate, styrene, and mixtures thereof. It is preferred that the initial monomer comprise at least 80% by weight, based on the weight of initial monomer, of monomer selected from methyl methacrylate, styrene, and mixtures thereof. Initial monomer comprising at least 50% by weight methyl methacrylate is especially preferred.

Examples of nonionic monoethylenically unsaturated monomers which may be employed in preparing the core/shell particle includes styrene, vinyl toluene, ethylene, vinyl acetate, vinyl chloride, vinylidiene chloride, acrylonitrile, (meth)acrylamide, various ($C_1$–$C_{20}$) alkyl or ($C_3$–$C_{20}$) alkenyl esters of (meth)acrylic acid; for example, methyl methacrylate, methyl acrylate, ethyl (meth)acrylate, butyl (meth)acrylate, 2-ethylhexyl (meth)acrylate, benzyl (meth)acrylate, lauryl (meth)acrylate, oleo (meth)acrylate, palmityl (meth)acrylate, and stearyl (meth)acrylate. The expression (meth)acrylic acid is intended to serve as a generic expression embracing both acrylic and methacrylic acid. Similarly, the expression (meth)acrylate is intended as a generic expression embracing both acrylic acid and methacrylic acid esters.

Examples of alpha, beta-ethylenically unsaturated carboxylic acid monomer which may be used to prepare the core/shell particles include acid monomers such as methacrylic acid, beta-acryloxypropionic acid, mixtures of beta-acryloxypropionic acid and higher oligomers of acrylic acid, methacryloxypropionic acid, itaconic acid, citraconic acid, crotonic acid, maleic acid or maleic anhydride, fumaric acid, monomethyl maleate, monomethyl fumarate and monomethyl itaconic, and mixtures thereof and mixtures of methacrylic and acrylic acids. The preferred acid monomers that may be employed in preparing the core particles of the present invention are methacrylic acid and mixtures of acrylic acid and methacrylic acid, especially preferred is methacrylic acid. It is preferred that the methacrylic acid comprise from about $2\frac{1}{4}$ to 3% by weight, based on the total weight of initial monomer, of the initial monomer. Other preferred acid monomers that may be used include acryloxypropionic acid, and mixtures of acryloxypropionic acid and the higher oligomers of acrylic acid.

It is preferred that the initial monomer used to prepare the core/shell particles comprise up to 10% by weight, based on the total weight of initial monomer, of monomer selected from the group consisting of ethyl acrylate, acrylonitrile and mixtures thereof. Ethyl acrylate is especially preferred. When ethyl acrylate is employed, it is preferred that about 5% by weight, based on the total weight of initial monomer, be used.

The hydrophobic solvent used in preparing the core particle is preferably selected from the acyclic paraffinic hydrocarbons, mixtures of the acyclic paraffinic hydrocarbons and cyclic paraffinic hydrocarbons and mixtures of acyclic paraffinic hydrocarbons, cyclic paraffinic hydrocarbons and aromatic hydrocarbons wherein the mixtures contain less than about 10% by weight, based on the total weight of the mixture, of aromatic hydrocarbons. Examples of hydrophobic solvents which may be employed include mineral spirits, petroleum spirits, ligroin, VM&P naphtha (varnish maker's and painter's naphtha), refined solvent naphtha, solvent naphtha, petroleum and petroleum benzin. It is preferred that the 50% distillation temperature of the hydrophobic solvent be from about 150° C. to 200° C. It is especially preferred that a hydrophobic solvent with a 50% distillation temperature of from about 150° C. to 180° C. be employed in the process of preparing the core particles. It is also preferred that the hydrophobic solvent be a mixture of acyclic paraffinic hydrocarbons and cyclic paraffinic hydrocarbons wherein the cyclic paraffinic hydrocarbons comprise no more than about 5% by weight of the mixture.

The hydrophilic solvent employed in preparing the core particle is preferably selected from the isomers of butanol, pentanol, hexanol, and methyl isobutyl carbitol and mixtures thereof. When the hydrophilic solvent is a hydroxyl compound, it is preferred that the proportion of hydrophilic solvent to hydrophobic solvent be chosen so that there are from about 0.28 to about 0.42 moles of hydroxyl functionality per 100 gms of hydrophilic/hydrophobic solvent blend. It is especially preferred that the proportion of hydrophilic to hydrophobic solvent be chosen to give 0.34 moles of hydroxyl functionality per 100 gms of solvent blend. For example, when pentanol is chosen as the hydrophilic solvent to be employed, the weight ratio of hydrophilic to hydrophobic solvent is preferably from about 1:3 to about 9:11, and a ratio of about 3 to 7 is especially preferred. When butanol is selected as hydrophilic solvent, a ratio of hydrophilic to hydrophobic solvent of about 1 to 3 is especially preferred. When hexanol is chosen as hydrophilic solvent, a weight ratio of hydrophilic to hydrophobic solvent of about 3.5 to 6.5 is especially preferred.

An anionic surfactant such as an alkali metal salt of a di($C_7$–$C_{25}$)alkylsulfosuccinates or of an alkyl aryl sulfonate, is employed as an aid in preparing the initial dispersion of initial monomer, solvent mixture (including organic target material, if desired), and emulsion stabilizer.

Examples of suitable anionic dispersing agents include, for example, the higher fatty alcohol sulfates, such as sodium lauryl sulfate, and the like; alkylaryl sulfonates such as sodium or potassium isopropylbenzene sulfonates or isopropyl naphthalene sulfonates, and the like; alkali metal higher alkyl sulfosuccinates, such as sodium octyl sulfosuccinate, sodium N-methyl, N-palmitoyltaurate, sodium oleyl isothionate, and the like; and alkali metal salts of alkylarylpolyethoxyethanol sulfates, sulfonates or phosphates, such as sodium tert-octylphenoxypolyethoxyethyl sulfates and nonyl phenoxypolyethoxy ethyl phosphates, either having 1 to 7 oxyethylene units, and the like. An example of a preferred alkali metal salt dioctylsulfosuccinate is sodium dioctyl sulfosuccinate. An example of a preferred alkylbenzene sulfonate is sodium dodecylbenzene sulfonate. It is preferred that the anionic surfactant comprise from about 0.2 to 0.8% by weight of the organic phase of the core emulsion. It is especially preferred that the anionic surfactant comprise from about 0.3 to 0.5% by weight of the organic phase of the core emulsion.

The water-insoluble emulsion stabilizer may be selected from organic compounds having a molecular weight of less than about 500 and a water solubility of less than about $10^{-4}$ gms per liter. The water-insoluble emulsion stabilizer is preferably selected from the di($C_4$–$C_{10}$)alkyl phthalates, dibutoxyethyl phthalate, n-butyl benzyl phthalate, dimethylcyclohexyl phthalate, dicyclohexyl phthalate, diphenyl phthalate, dipropeneglycol dibenzoate, diethyleneglycol dibenzoate, triethyleneglycol di-(2-ethylbutyrate), di-(2-ethylhexyl) adipate, di-isooctylazelate, di-(2-ethylhexyl)azelate, di-n-butyl sebacate, 1-chlorododecane, hexadecane, and mixtures thereof. An especially preferred water-insoluble emulsion stabilizer is di(2-ethylhexyl)phthalate (a/k/a dioctyl phthalate). It is preferred that the water-insoluble emulsion stabilizer comprise at least about 0.25% by weight of the organic phase of the core emulsion. It is especially preferred that the water-insoluble emulsion stabilizer comprise from about 2.5 to 4% by weight of the organic phase of the core emulsion.

The core emulsion contains a water-insoluble thermal polymerization initiator such as lauryl peroxide. The ratio of the weight of the water-insoluble thermal polymerization initiator to the total weight of initial monomer employed in preparing the core emulsion is from about 0.1:100 to 5:100. It is preferred that the ratio of the weight of the water-insoluble thermal polymerization initiator to the total weight of the initial monomer be from about 2.5:100 to 4:100.

The core emulsion is prepared by adding the solvent blend, initial monomer, emulsion stabilizer, anionic surfactant and water-insoluble initiator to water and subjecting the mixture to high mechanical shearing forces. The shear force may be applied mechanically as by use of a high shear mechanical disperser such as a Waring ® Blender (Waring is a trademark of Dynamic Corp. of America) or high speed impeller as are commonly used in coatings manufacture. Alternatively, the high shear dispersion may be accomplished ultrasonically. The average particle size and particle size distribution of the core emulsion is believed to depend upon the magnitude and duration of the shearing forces applied.

In addition, the particle size distribution is believed to depend on the nature and relative amount of anionic surfactant used, the nature and amounts of the solvents employed, the nature and relative amounts of the monomers to be copolymerized, and the like.

When the polymerized dispersion is to ultimately be used to impart opacity, it is preferred that the average particle size of the core emulsion after dispersion be from about 0.22 to 0.35 microns as determined by photon correlation spectroscopy. Light scattering techniques such as photon correlation spectroscopy measure the Z-average particle size. It is especially preferred that the average particle size of the core emulsion after dispersion be from about 0.27 to 0.32 microns, when the polymerized dispersion resulting from the core emulsion is to be used to impart opacity, as in coating compositions.

After the core emulsion has been formed, it is heated to activate the thermal water-insoluble polymerization initiator. The optimum polymerization temperature depends upon the thermal initiator used to effect the polymerization. When lauryl peroxide is employed the core emulsion is preferably heated to a temperature of from about 86° to 89° C. Because the initial monomer and hydrophobic/hydrophilic solvent blend are chosen so that the polymer is formed from the initial monomers insoluble in the solvent blend, it is believed that the polymer forms a separate phase within the core emulsion when the initial monomer is polymerized. After polymerization of the initial monomer, the copolymerized residues of the acid monomer are neutralized by addition of a base selected from ammonia and a organic amines. Ammonia is preferred to effect the neutralization.

Subsequent to the neutralization of the polymerized carboxylic acid, additional monomer may be added to the core/shell particles. It is preferred that the additional monomer be selected to yield polymer having a calculated glass transition temperature greater than about 80° C. Any of the non-carboxylic acid monomers useful in preparing the core polymer may be employed as additional monomer. Thus, for example, ethyl acrylate, butyl acrylate, methyl methacrylate, styrene, and acrylonitrile may be employed. Mixtures of ethylenically unsaturated monomers, such as methyl methacrylate, butyl acrylate, and methyl methacrylate styrene mixtures may be used. Methyl methacrylate is preferred. It is especially preferred that the additional monomer comprise at least about 80% by weight, based on the total weight of the additional monomer, of methyl methacrylate.

The additional monomer may also comprise at least one multi-alpha, beta-ethylenically unsaturated monomer. It is preferred that when such multi-alpha, beta-ethylenically unsaturated monomer is employed it comprise no more than about 5% by weight of the total additional monomer. Preferred multi-alpha, beta-ethylenically unsaturated monomers useful as additional monomer are allyl (meth)acrylate, tripropyleneglycol di(meth)acrylate, diethyleneglycol di(meth)acrylate, ethyleneglycol di(meth)acrylate, 1,6-hexanediol di(meth)acrylate, 1,3-butyleneglycol di(meth)acrylate, diallyl phthalate, trimethylolpropane tri(meth)acrylate, and divinylbenzene. Especially preferred multi-alpha, beta-ethylenically unsaturated monomers are allyl methacrylate, diallyl phthalate, and trimethylolpropane trimethacrylate.

It is preferred that the weight ratio of solvent blend (that is hydrophilic plus hydrophobic solvents) to initial monomer be from about 1:0.8 to 1:3. It is especially preferred that the ratio of solvent blend to initial monomer be about 1:1.3. It is preferred that the weight ratio of initial monomer to additional monomer be from about 0.9 to 1.5. It is especially preferred that the weight ratio of initial monomer to additional monomer be about 1.3:1.

The core/shell particles prepared by the process of the present invention are useful as opacifying agents in coating compositions. Drying compositions which contain aqueous dispersions of these core/shell particles is believed to cause the formation of single individual voids within the core/shell particles which contribute to the opacity of the dried compositions containing the core/shell particles. When the core/shell particles of the present invention are used as opacifying agents, the amount of polymer deposited to form the shell polymer is generally such so as to provide an overall particle size of the core/shell particle of from about 0.35 to 0.55 microns, preferably from about 0.42 to 0.48 microns, and a polydispersity index of from about 1.5 to 5.

The core/shell particles of the present invention are useful for aqueous coating and impregnating compositions such as those of U.S. Pat. No. 2,795,564, as opacifying agents and such compositions either as a supplement to, or replacement of, pigmentary matter and/or extenders therefor. For these purposes the aqueous dispersions of the core/shell polymer may be added directly to the coating and or impregnating compositions. Alternatively, the core/shell polymers may be isolated from the dispersions, by filtration or decantation, and then the organic solvent blend may be removed as by drying or volatilization, under conditions such that microvoids are formed and retained in the individual particles or granules, the latter being more or less free flowing in character so that they can be packaged, shipped or stored before use. The dry powder thus obtained can also be used in coatings based on organic solvents provided that the shell component of the core/shell particles is not soluble in the organic solvent.

Besides being useful in water-based paints based on vinyl or acrylic polymer lattices or aqueous solutions of vinyl or acrylate polymers, to replace all or part of opacifying pigments heretofore used, especially titanium dioxide, microvoid containing core/shell particles polymers of the present invention may be used for similar purposes in other coating systems, including resin formaldehyde condensation products of thermosetting type, such as phenoplast and aminoplast, including urea formaldehyde, and melamine formaldehyde, and other condensates, for example, water dispersible alkyd resins.

An opacified composition adapted for coating and/or impregnanting a surface may comprise an aqueous dispersion of water-insoluble emulsion vinyl addition polymer having an apparent $T_g$ of from about 5° to 25° C., and water-insoluble core shell particles of the present invention at a pigment volume concentration of at least about 5%, inorganic pigment, such as titanium dioxide, and optional extender.

In another embodiment the process of the present invention may be employed to encapsulate organic target materials such as organic compounds, which are relatively insoluble in water but soluble in the blend of solvent and monomer used to prepare the core emulsion. The material to be encapsulated is included in the mixture used in preparing the core emulsion. Examples of organic target materials which may be encapsulated by the process of the present invention include pesticides, biocides, herbicides, fungicides, insecticides, dyes, inks, colorants, chelating agents, perfumants, pharmaceuticals and the like. Any liquid, solvent-soluble solid, or the like which is sufficiently hydrophobic, so that when mixed with aqueous dispersion of core emulsion it tends to became substantially distributed within the core emulsion phase, and does not inhibit polymerization of the core emulsion, may be microencapsulated by the present technique. Aqueous dispersions of microencapsulated pesticides, biocides, herbicides, fungicides, insecticides, and pharmaceuticals are especially useful in preparing controlled release formulations, in which the encapsulated material is slowly released from the microcapsule, as by diffusion through the microcapsule walls. Aqueous dispersions of microencapsulated pesticides, biocides, herbicides, fungicides, insecticides and the like may be included with other agricultural chemicals such as emulsifiable concentrates of pesticides in tank mixes and sprayed using conventional application equipment. Microencapsulation may result in reduced toxicity and extended effective application lifetime for pesticides and other toxic materials.

Examples of organic target compounds with biocidal activity include water-insoluble herbicidal diphenyl ethers such as oxyfluorfen and water-insoluble isothiazolone biocides such as 2-n-octyl-3-isothiazolone.

When employed to encapsulate inks, dyes and colorants and the like, the core/shell particles of the present invention may be released by application of mechanical force to the core/shell particles, or which otherwise breaks, melts, dissolves or otherwise destroys the integrity of the microcapsule shell. Alternatively, the shell of the core/shell polymer shell may be permeable to the target organic compound, resulting in slow continuous release of the target material from the core/shell particles.

Core/shell particles of the present invention encapsulating target organic materials such as biocides may be used to prepare microbe resistant coatings compositions, and especially water-based coatings compositions. For example, biocide encapsulated in an aqueous dispersion of water-insoluble core/shell particles of the present invention may be mixed with pigments, extenders, vinyl addition latex polymer, and the like, to form a coating composition. Core/shell particles may be prepared which both contribute opacity to the film formed by the coating composition in which they are included and slowly release biocidally active material to help preserve the coating film from microbial attack.

When employed to encapsulated target materials, it is preferred that ratio of solvent to monomer blend used to prepare the core particles be about 1:2.7.

In preparing microencapsulated target materials, a single stage process which does not employ additional monomer is preferred.

Core/shell particles of the present invention may also be prepared in the presence of an organic target material containing chemically reactive functional groups such as isocyanate functional groups and epoxy groups.

The following abbreviations are used in the examples below:
EA—ethyl acrylate
MMA—methyl methacrylate
AN—acrylonitrile
MAA—methacrylic acid
S—styrene
BA—butyl acrylate
ALMA—allyl methacrylate The following examples are illustrative of the present invention which is in no way limited thereby. In the examples the parts and percentages are by weight and temperatures are in degrees Celsius unless otherwise stated.

EXAMPLE 1

Preparation of Core/Shell Particles

A core emulsion is prepared by adding, to 200 parts of water, 100 parts of a solvent mixture composed of 70 parts Isopar G isoparaffin hydrocarbons (Isopar is a trademark of Exxon) and 30 parts n-pentanol, 100 parts of the initial (first stage) monomer mixture (5 parts ethyl acrylate, 92.5 parts methyl methacrylate, and 2.5 parts methacrylic acid), 6 parts of dioctylphthalate, 0.85 parts Monowet MO-70E surfactant (Monowet is a trademark of Mono Industries, Inc.) and 3.5 parts Alperox F lauryl peroxide (Alperox is a trademark of Pennwalt). The mixture is then emulsified at high shear (18,000 rpm) using a Micro-Mixer emulsifier, (manufactured by Charles Ross & Son Company, Hauppauge, N.Y.) for 7-10 minutes. 300 parts of core emulsion is mixed with 75 parts of water at room temperature in a 4-neck-round bottom flask equipped with a stirrer, thermometer and temperature regulator, condenser, and nitrogen stream. Under nitrogen, the temperature of the reaction mixture is raised to 85°-87° C. and this temperature is maintained for ½ hour. 6.5 parts of ammonia (5.6%) is then added through one of the necks and the reaction mixture is stirred for ½ hour. Gradual addition of the additional (second stage) monomer mixture is then begun. The second stage monomer mixture contains 10 parts butyl acrylate, 87 parts methyl methacrylate and 2 parts allyl methacrylate. 73 parts of this mixture are gradually added over a 90-100 minute period to the reaction flask containing the initial core/shell particles. One-half hour after initiating the second stage monomer feed, 2.2 parts of dilute ammonia (5.6%) are added to the reaction flask. One hour after the second stage monomer feed is initiated another 2.2 parts of dilute ammonia (5.6%) is added. After the second stage monomer mixture feed has been completed, the temperature of the reaction flask is maintained for ½ hour. The reaction mixture is then cooled and decanted from the reaction flask.

Preparation of Polymer Film and Measurement of Opacity

An aqueous dispersion of core/shell particles is mixed with a commercially available film-forming acrylic latex polymer, RHOPLEX® AC-64 polymer (RHOPLEX is a trademark of Rohm and Haas Company), in a 15-85 ratio (based on the weight of solids of each polymeric dispersion). The mixture of core/shell particles and film-forming latex polymer particles is diluted to a final total solids of 40%. A film is drawn down over black polyvinyl chloride sheets having a matte finish using an applicator having a 5 mil (0.0127 cm) aperture to give a nominal film thickness of 5 mils. Two draw downs are made, one for drying under low relative humidity (approx. 30%), the other under high humidity (about 70%). The two films are dried overnight. Light scattering from the dried films is then measured using a Gardner Colorgard 45% Reflectometer (Gardner Laboratories, Inc.). Kubelka-Munk scattering coefficients (s/ml) are calculated for the dried films by the method of P. B. Mitton and A. E. Jacobsen, *Official Digest*, Vol. 35, Federation of Paint and Varnish Production Clubs, ODFPA, September 1963, pp 871-911.

Using the method of Example 1 above, aqueous dispersions of core/shell particles were prepared and their ability to opacify a model film was measured as described above.

Table I reports the results of varying the monomer composition of the first stage on the film opacity for core/shell particles prepared using the process of Example 1.

TABLE I

Effect of First Stage Monomer Composition on Film Opacity

| Example | First Stage[2] Composition | Film Opacity S/mil | % Collapse |
|---|---|---|---|
| 1 | 5 EA/92.5 MMA/2.5 MAA | .439 | 3 |
| 2 | 10 BA/87.5 MMA/2.5 MAA | .336 | 34 |
| 3 | 10 EA/87.5 MMA/2.5 MAA | .397 | 31 |
| 4 | 97.5 MMA/2.5 MAA | .371 | 21 |
| 5 | 5 AN/92.5 MMA/2.5 MAA | .362 | 17 |
| 6 | 5 S/92.5 MMA/2.5 MAA | .400 | 19 |

[1]The process used employs solvent (hydrophobic plus hydrophilic), initial monomer (first stage), and additional monomer (second stage) in a weight ratio of 1:1:1. The solvent is a mixture of Isopar G isoparaffins and n-pentanol in a weight ratio of 7:3. 0.3% Monowet MO-70E surfactant (based on the weight of the organic phase in the initial stage) is employed.

[2]Second stage monomer composition is 10 BA/88 MMA/2.0 ALMA.

[3]The % collapse is determined as follows: $\frac{(S/mil)30\% - (S/mil)70\%}{(S/mil)30\%}$ The data in Table II give the effect of varying the composition of the second stage of the core/shell particles on film opacification.

TABLE II

Effect of Second Stage Monomer Composition on Film Opacity

| Example | Monomer Composition[1] Stage I | Stage II | Opacity S/mil | % Collapse[2] |
|---|---|---|---|---|
| 2 | 10 BA/87.5 MMA/2.5 MAA | 10 BA/88 MMA/2 ALMA | .336 | 34 |
| 7 | 5 S/92.5 MMA/2.5 MAA | 10 BA/88 MMA/2 ALMA | .400 | 19 |
| 8 | 5 S/92.5 MMA/2.5 MAA | 10 EA/88 MMA/2 ALMA | .382 | 14 |
| 9 | 5 S/92.5 MMA/2.5 MAA | 5 S/93 MMA/2 ALMA | .409 | 9 |
| 10 | 5 EA/92.5 MMA/2.5 MAA | 5 S/93 MMA/2 ALMA | .349 | 10 |

[1]The process used employs solvent (hydrophobic plus hydrophobic), initial monomer (first stage), and additional monomer (second stage) in a weight ratio of 1:1:1. The solvent is a mixture of Isopar G isoparaffins and n-pentanol in a weight ratio of 7:3. 0.3% Monowet MO-70E surfactant (based on the weight of the organic phase in the initial stage is employed.

[2]The % collapse is determined as follows: $\frac{(S/mil)30\% - (S/mil)70\%}{(S/mil)30\%}$.

Table III gives the effect of varying the solvent blend on the properties of core/shell particles prepared by the process of Example 1.

TABLE III

Effect of Hydrophobic Solvent on Film Opacity[1]

| | | Solvent Properties | | | | | |
| | | | Composition (%) | | | Film Properties | |
| Example | Solvent | 50% Dist. Temp. | Paraf | Cyclo-paraf. | Arom. | S/mil | % Collapse[7] |
|---|---|---|---|---|---|---|---|
| 11 | Odorless Mineral Spirits | 183 | 86 | 14 | | .222 | 32 |
| 12 | Mineral Spirits 66/3 | 172 | 48 | 51 | | .219 | 14 |
| 13 | Isopar G[3] | 163 | 93 | 7 | | .249 | 10 |
| 14 | Isopar H[3] | 181 | 94 | 7 | | .217 | 31 |
| 15 | Norpar 12[4] | 200 | 98 | 2 | | .268 | 41 |
| 16 | Varsol[5] | 172 | 46 | 40 | 14 | .169 | 34 |

TABLE III-continued

Effect of Hydrophobic Solvent on Film Opacity[1]

| Example | Solvent | Solvent Properties 50% Dist. Temp. | Composition (%) Paraf | Cyclo- paraf. | Arom. | Film Properties S/mil | % Collapse[7] |
|---|---|---|---|---|---|---|---|
| 17 | VM&P Naphtha[6] | 122 | 49 | 41 | 10 | .028 | — |

[1]The process used to prepare the aqueous dispersions of core/shell particles employes solvent, initial monomer and additional monomer in a weight ratio of 1:1.3:1. The solvent is a mixture of n-pentanol and hydrophobic solvent in a weight ratio of 3:7. The monomer composition of Example 1 is used in preparing the core/shell particles.
[2]"Mineral spirits 66/3" refers to Amsco Mineral Spirits 66/3; from Union Chem. Div. of Union Oil Company.
[3]Isopar is a trademark of Exxon.
[4]Norpar is a trademark of Exxon. Norpar 12 solvent is a mixture of highly pure normal parraffins, and has 13% by weight C-10, 36% C-11, 44% C-12, and 7% C-13 alkanes.
[5]Varsol is a trademark of Exxon.
[6]VM&P naphtha is a narrow boiling fraction of petroleum.
[7]See footnote 2 of Table II.

Table IV gives the effect of varying the methacrylate acid level in the first stage on the film opacification for core/shell particles prepared using the process of Example 1.

TABLE IV

Effect of Methacrylic Acid Level on Film Opacity

| Example | % MAA[1] | S/Mil | % Collapse[2] (high % RH) |
|---|---|---|---|
| 18 | 2.0 | .02 | (41)[4] |
| 19 | 2.5 | .22/.25 | 32/7 |
| 20 | 3.0 | .20 | 35 |
| 21 | 3.5 | .02 | (73)[5] |

[1]The process used to prepare aqueous dispersion of core/shell particles employs solvent, initial monomer and additional monomer in a weight ratio of 1:1.3:1. A solvent blend of odorless mineral spirits and n-pentanol in a weight ratio of 7:3 is used. Example 18 has an initial monomer composition of 10 BA/88 MMA/2 MAA and an additional monomer composition of 10 BA/88 MAA/2 ALMA. In the succeeding examples, as the level of MAA is increased, the level of MMA is correspondingly decreased.

[2]The % collapse is determined as follows: $\frac{(S/mil)30\% - (S/mil)70\%}{(S/mil)30\%}$ Table V gives the effect of varying the allyl methacrylate level in the second stage composition on the film opacification of core/shell particles prepared according to the process of Example 1.

TABLE V

Effect of ALMA Level on Film Opacity

| Example | % ALMA[1] | S/Mil | % Collapse[2] |
|---|---|---|---|
| 22 | 0 | .201 | 27 |
| 23 | 0.5 | .213 | 18 |
| 24 | 1 | .235 | 22 |
| 25 | 2 | .247 | 7 |
| 26 | 3 | .192 | 32 |
| 27 | 4 | .212 | 29 |

[1]The process used to prepare aqueous dispersions of core shell particles employs solvent, initial monomer and additional monomer in a weight ratio of 1:1.3:1. A solvent blend of colorless mineral spirits and n-pentanol in a weight ratio of 7:3 is used. Example 22 has an initial monomer composition of 10 BA/87.5 MMA/2.5 MAA and an additional monomer composition of 10 BA/90 MMA. In the succeeding examples, as the level of ALMA is increased, the level of MMA is correspondingly decreased.
[2]The % Collapse and Calculated Shell Thickness and Void Volume are determined as for Examples 18-21 above.

Table VI gives the effect of varying the level of surfactant employed in the process of Example 1 on the film opacification of the core/shell particles produced.

TABLE VI

Effect of Surfactant Level on Film Opacity

| Example | % Surfactant/Org. Phase | S/Mil | % Collapse (high % RH) |
|---|---|---|---|
| 28 | 0.3 | .243 | 35 |
| 29 | 0.4 | .264 | 19 |
| 30 | 0.5 | .290 | 33 |
| 31 | 0.65 | .244 | 24 |
| 32 | 0.8 | .222/.247 | 32/7 |

[1]The process used to prepare aqueous dispersion of core/shell particles employs solvent, initial monomer and additional monomer in a weight ratio of 1:1.3:1. A solvent blend of odorless mineral spirits and n-pentanol in a weight ratio of 7:3 is used. The monomer composition is the same as Example 2 above. Example 28 is prepared using 0.3% Monowet MO-70E surfactant as a weight percentage of the organic phase in the initial polymerization stage.
[2]The % Collapse, is determined as for Examples 18-21 above.

EXAMPLE A

Encapsulation of Methyl Hexanoate

A core emulsion is prepared by adding, to 233 parts of water, 100 parts of a solvent mixture (55 parts Isopar G isoparaffins/30 parts n-pentanol/15 parts methyl hexanoate), 133 parts of monomer mixture (97.5 parts methyl methacrylate/2.5 parts methacrylic acid), 7 parts dioctyl phthalate, 1 part of Monowet-70E surfactant, and 4.7 parts of Alperoxide-F lauryl peroxide initiator. The mixture is then emulsified by mixing at high shear (18,000 rpm) for 10 minutes using a Ross Micro-Mixer Emulsifier. 250 parts of the core emulsion is transferred to a reaction vessel consisting of a 4-neck round-bottom flask equipped with a stirrer, thermometer and temperature regulator, condenser and a nitrogen stream. 62.5 parts of water is added to the reaction flask. Under nitrogen the temperature of the reaction mixture is brought to 85°–88° C. and maintained at that temperature for ½ hour. 6.2 parts of diluted ammonia (5.6%) is then added and the temperature is maintained for another ½ hour. Gradual addition of additional (second stage) monomer mixture is then begun. The monomer mixture consists of 52.2 parts of a mixture of 98 parts methyl methacrylate to 2 parts of allyl methacrylate. The second stage mixture is added over a period of approximately 75 minutes. Approximately 25 minutes after beginning the gradual addition of second stage monomer, 2.1 parts of dilute ammonia (5.6%) is added. Approximately 50 minutes after initiating the gradual addition of second stage monomer another 2.1 parts of dilute ammonia (5.6%) is added. The temperature of the reaction flask is maintained for 30 minutes after completion of the second stage monomer feed after which the reaction flask is cooled and the aqueous dispersion of core/shell particles is decanted. The core/shell particles of this preparation give a film opacity of 0.28 s/mil. The hydrolysis rate of the encapsulated methyl hexanoate was measured at a pH of 11.5 using gas liquid chromatography. The half life of the encapsulated ester was 83 minutes in comparison with the half life of 17 minutes for unencapsulated ester.

EXAMPLE B

Encapsulation of SKANE Biocide

A core emulsion is prepared by adding to 367 parts of water 100 parts of a solid mixture composed of 55 parts odorless mineral spirits, 30 parts n-pentanol and 15 parts SKANE M-8 (SKANE is a trademark of Rohm and Haas Company) biocide. 268 parts of a monomer mixture composed of 10 parts butyl acrylate, 88.5 parts methyl methacrylate and 2.5 parts methacrylic acid are added, as are 11 parts dioctyl phthalate, 2.6 parts Monowet MO-70E surfactant, and 9.3 parts lauroyl peroxide initiator. The mixture is then emulsified at high speed (18,000 rpm) using a Ross Micro-Mixer Emulsifier for 10 minutes. 250 parts of the core emulsion is transferred to a reaction vessel as in Example 1. 62.5 parts of water is added to the reaction vessel. Under nitrogen the temperature of the reaction mixture is brought to 85°-88° C. and the temperature is maintained for 60 minutes. 7.8 parts of dilute ammonia (5.6%) are then added and the temperature is maintained at 85°-88° C. for an additional 30 minutes. The reaction mixture is then cooled and decanted. Example B is repeated except that a solvent mixture of 40 parts odorless mineral spirits, 30 parts n-pentanol and 30 parts SKANE biocide is employed yielding Example B-1.

Aqueous latex paint is prepared according to the following formulation:

| Materials | Parts by Weight |
|---|---|
| water | 58 |
| methyl CARBITOL | 59 |
| QR-681M dispersant | 7.1 |
| TRITON ® N-57 surfactant | 4.0 |
| Colloid 643 defoamer | 1.0 |
| TiPure R-902 titanium dioxide | 225 |
| Minex 4 pigment | 160 |
| Icecap K pigment | 50 |

The above ingredients are ground at high speed (3800-4500 rpm) for 10-15 minutes and the let down at slower speed with the following additional ingredients.:

| water | 50 |
|---|---|
| Rhoplex AC-64 polymer emulsion | 306 |
| Colloid 643 defoamer | 3.0 |
| Texanol coalescent | 9.0 |
| NH4OH | 2.9 |
| Natrosol 250 MHR thickener | 199.6 |
| water | 22.1 |
| Formulation Constants | |
| Initial viscosity, KU | 88 |
| pH | 9.5 |

QR-681M is a dispersant and a product of Rohm and Haas Company.
TRITON ® N-57 surfactant is a product of Rohm and Haas Company. CAS Registry No. 9016-45-9
Colloid 643 is an antifoam agent and a product of Colloids, Inc.
TiPure R-902 titanium dioxide is a product of E. I. DuPont De Nemours Co.
Minex 4 clay is a product of Indusmin Co.
Icecap K is a product of Burgess Pigment Co.
RHOPLEX ® AC-64 polymer latex emulsion is a product of Rohm and Haas Company.
Natrosol 250 MHR cellulosic thickener is a product of Hercules, Inc.

This paint was spiked with encapsulated biocide of Example B to provide a test paint with 2 grams of active ingredient/1200 gms of paint.

Table VII gives the result of encapsulating the biocide on its heat-age stability in paints. The heat-aged stability is measured by placing the test paint in a 60° C. oven for aging. At appropriate intervals samples are taken and analyzed for SKANE M-8 biocide via a GLC technique.

TABLE VII

% of Initial Skane M-8 Biocide Remaining

| First Series | | Second Series | | | |
|---|---|---|---|---|---|
| Days at 60° C. | Uncapsulated Biocide | Encapsulated 15% | Days at 60° C. | Unencapsulated Biocide | Encapsulated |
| | | | | | 15%[1] | 30%[1] |
| 0 | 100 | 100 | 0 | 100 | 100 | 100 |
| 4 | 81.5 | 100 | 5 | 32 | 100 | 100 |
| 7 | 0 | 100 | 9 | 0 | 100 | 100 |
| 10 | — | 99 | 12 | | 100 | 100 |
| 13 | | 100 | | | 100 | |
| 16 | | 99 | 16 | | 100 | 52 |
| 20 | | 99 | 20 | | 100 | 0 |
| 24 | | 84 | | | 100 | |
| 27 | | 91 | 26 | | 100 | |
| | | | 30 | | 100 | |
| 31 | | 76 | | | 100 | |
| | | | 35 | | 100 | |
| | | | 40 | | 100 | |
| | | | 44 | | 100 | |
| | | | 51 | | 45 | |

[1]% SKANE M-8 biocide on solvent core.

The results in Table VII indicate that encapsulation of the biocide by the process of present invention increases the heat-age stability of the biocide in paint compositions. Heat-age stability is believed to be predictive of long-term room temperature storage stability of paint formulations.

EXAMPLE C

Encapsulation of GOAL ® Herbicide

A core emulsion is prepared by adding to 368 parts of water 100 parts of solvent mixture consisting of 45 parts Isopar G, isoparaffins, 30 parts n-pentanol and 25 parts technical grade GOAL oxyfluorfen herbicide (GOAL is a trademark of Rohm and Haas Company). 270 parts of a monomer mixture (5 parts ethyl acrylate/92.5 parts methyl methacrylate/2.5 parts methacrylic acid) is added to the core emulsion mixture as are 11 parts dioctyl phthalate, 2.5 parts Monowet MO-70E surfactant, and 9.4 parts Alperoxide F lauryl peroxide initiator. The mixture is then emulsified at high shear (18,000 rpm) for about 7 to 10 minutes using a Ross Micro-Mixer Emulsifier.

250 parts of the core emulsion are transferred to the reaction vessel of Example 1 and 24.2 parts of water is added. Under nitrogen the temperature of the reaction mixture is brought to 85°-88° C. and there maintained for 60 minutes. Subsequently 7.8 parts of dilute ammonia (5.6%) is added to the reaction mixture and the temperature is maintained for another 30 minutes after which the reaction mixture is cooled and decanted to give Example C-1.

The same procedure is repeated substituting 50 parts by weight and 70 parts by weight of GOAL herbicide to yield Examples C-2 and C-3 respectively.

The procedure of Example C is repeated substituting (15% by weight on Isopar G/n-pentanol core solvent) a haloketone herbicide disclosed in U.S. Pat. No. 3,661,991, namely N-(1-methyl-1-ethyl-3-chloroacetonyl)-3,5-dichlorobenzamide, yielding Example D.

The procedure of Example C is repeated substituting (15% by weight on Isopar G/n-pentanol core solvent) a triazole fungicide, namely, alpha-(4-chlorophenyl)-butyl-1H-1,2,4-triazole-propanenitrile yielding Example E.

We claim:

1. An encapsulant composition comprising an aqueous dispersion of water-insoluble core/shell particles having a solvent core prepared by the process comprising:
   (a) preparing core emulsion by emulsifying in water at high shear constituents comprising
      (1) organic target material to be encapsulated,
      (2) at least one hydrophilic solvent,
      (3) initial monomer comprising at least two polymerizable mono-alpha, beta-ethylenically unsaturated compounds wherein said initial monomer includes from about 2 to 4 percent by weight, based on total weight of said initial monomer, of alpha, beta-ethylenically unsaturated carboxylic acid monomer,
      (4) hydrophobic anionic surfactant
      (5) water-insoluble emulsion stabilizer
      (6) water-insoluble thermal polymerization initiator, and wherein said organic target material and hydrophilic solvents are non-solvents for polymer prepared by polymerizing said initial monomer,
   (b) heating said core emulsion to polymerize said initial monomer, thereby forming core particles,
   (c) adding at least one base selected from the group consisting of ammonia and the organic amines thereby neutralizing polymerized carboxylic acid and forming core/shell particles having a solvent core and
   (d) optionally adding additional monomer whereby said additional monomer is polymerized on said core/shell particles having a solvent core.

* * * * *